United States Patent
Mook et al.

(10) Patent No.: US 10,989,720 B2
(45) Date of Patent: Apr. 27, 2021

(54) METHOD FOR CLINICALLY AND PATHOLOGICALLY MONITORING ALZHEIMER'S DISEASE THROUGH CONCENTRATION OF AMYLOIDBETA IN PLASMA

(71) Applicant: Seoul National University R&DB Foundation, Seoul (KR)

(72) Inventors: Inhee Mook, Seoul (KR); Jong-Chan Park, Seoul (KR); Hyun Jin Cho, Suwon-si (KR); Sun-Ho Han, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 760 days.

(21) Appl. No.: 15/570,186

(22) PCT Filed: Apr. 30, 2016

(86) PCT No.: PCT/KR2016/004572
§ 371 (c)(1),
(2) Date: Oct. 27, 2017

(87) PCT Pub. No.: WO2016/175625
PCT Pub. Date: Nov. 3, 2016

(65) Prior Publication Data
US 2018/0136234 A1    May 17, 2018

(30) Foreign Application Priority Data
Apr. 30, 2015   (KR) .................... 10-2015-0061626

(51) Int. Cl.
*G01N 33/48* (2006.01)
*G01N 33/50* (2006.01)
(Continued)

(52) U.S. Cl.
CPC .......... *G01N 33/6896* (2013.01); *A61B 5/15* (2013.01); *C07K 14/4711* (2013.01);
(Continued)

(58) Field of Classification Search
CPC ...... G01N 33/6896; G01N 33/68; G01N 1/30; G01N 1/10; C07K 14/81; C07K 14/4711;
(Continued)

(56) References Cited

U.S. PATENT DOCUMENTS

| 6,913,932 | B2 * | 7/2005 | Maples | ........... A01N 1/02 252/408.1 |
| 2013/0259847 | A1 * | 10/2013 | Vishnudas | ........... A61P 29/00 424/94.1 |

OTHER PUBLICATIONS

Georganopoulou et al., "Nanoparticle-based detection in cerebral spinal fluid of a soluble pathogenic biomarker for Alzheimer's disease", PNAS, vol. 102, No. 7, pp. 2273-2276, (2005).
(Continued)

*Primary Examiner* — Russell S Negin
(74) *Attorney, Agent, or Firm* — Vorys, Sater, Seymour & Pease LLP; Muh Suhn Koh

(57) ABSTRACT

Provided is a method for quantifying Aβ in plasma by treating the plasma with MPP and/or TCEP, and a method for diagnosing, using the quantifying method, whether or not clinical cognitive deterioration and pathological Aβ accumulation occur. Through cut-off values of measured values measured by the method for quantifying Aβ according to the present subject matter, it is possible to identify normal, MCI and AD subjects and determine whether or not accumulation of Aβ in the brain occurs, and it is possible to predict progression to AD.

6 Claims, 11 Drawing Sheets

(51) Int. Cl.

| | |
|---|---|
| *G01N 33/68* | (2006.01) |
| *G01N 1/10* | (2006.01) |
| *C07K 14/81* | (2006.01) |
| *G01N 1/30* | (2006.01) |
| *G16H 50/20* | (2018.01) |
| *G16H 50/30* | (2018.01) |
| *A61B 5/15* | (2006.01) |
| *G16H 10/40* | (2018.01) |
| *C07K 14/47* | (2006.01) |

(52) U.S. Cl.
CPC .............. *C07K 14/81* (2013.01); *G01N 1/10* (2013.01); *G01N 1/30* (2013.01); *G01N 33/68* (2013.01); *G16H 10/40* (2018.01); *G16H 50/20* (2018.01); *G16H 50/30* (2018.01)

(58) Field of Classification Search
CPC ........ G16H 50/20; G16H 50/30; G16H 10/40; A61B 5/15
See application file for complete search history.

(56) References Cited

OTHER PUBLICATIONS

McKhann et al., "Clinical diagnosis of Alzheimer's disease: Report of the NINCDS-ADRDA Work Group under the auspices of Department of Health and Human Services Task Force on Alzheimer's Disease", Neurology, vol. 34, pp. 939-944, (1984).

Pitschke et al., "Detection of single amyloid β-protein aggregates in the cerebrospinal fluid of Alzheimer's patients by fluorescence correlation spectroscopy", Nature Medicine, vol. 4, No. 2, pp. 832-834, (1998).

\* cited by examiner

FIG. 4A
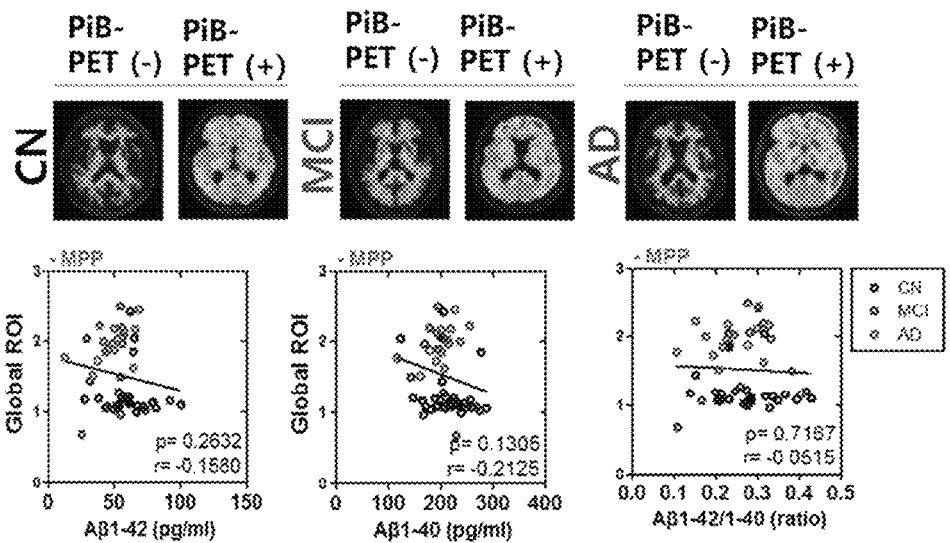
FIG. 4B
FIG. 4C
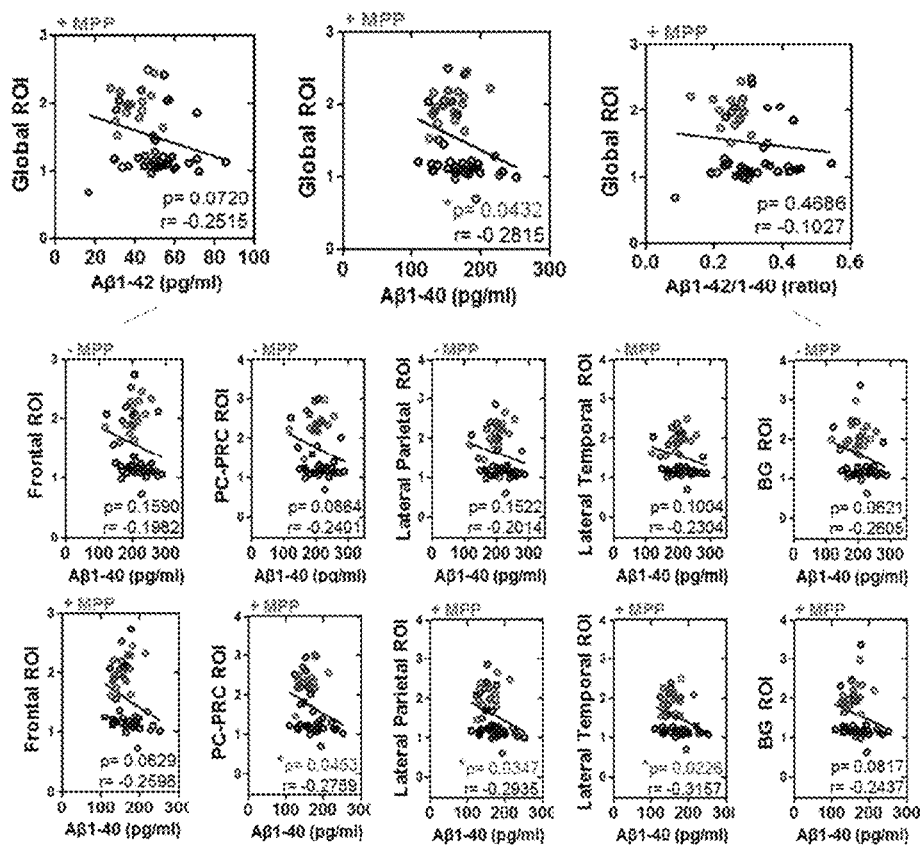

Lyophilized MPP

METHOD FOR CLINICALLY AND PATHOLOGICALLY MONITORING ALZHEIMER'S DISEASE THROUGH CONCENTRATION OF AMYLOIDBETA IN PLASMA

BACKGROUND OF THE INVENTION

Field of the Invention

The present disclosure relates to methods of monitoring the progression of Alzheimer's disease by determining the clinical cognitive deterioration and pathological accumulation of Aβ comprising treating a plasma sample with MPP (Mixture of protease inhibitors and phosphatase inhibitors) and/or TCEP; and measuring Aβ in the plasma.

Description of the Related Art

Alzheimer's disease (AD) is a neurodegenerative disease characterized by significant impairment of memory and other cognitive abilities (McKhann et al., Neurology 34; 939(1984)) and is considered a major cause of dementia. Dementia is a representative age-related neurodegenerative disease associated with the progressive loss of memory and other cognitive functions, in which the patients show a progressive impairment of the brain function resulting in the reduced or loss of memory, cognition and other behaviors or activities. The disease is known to be caused by the accumulation of Aβ (Amyloid beta, or Abeta) with toxicity. The accumulated Aβ causes death and damages to the cells of the brain, resulting in the malfunction of the brain. In Korea, about 290,000 people, accounting for about 9.5% of the people aged over 65, suffer from senile dementia, among which 180,000, accounting for 73% of the patients, are classified as being severe showing symptoms such as wondering around aimlessly. The number of the patients is expected to increase continuously with the increase of the aging population. By 2020, the number is expected to increase 2.4 fold to 700,000 people, compared to the present. AD and vascular dementia account for about 85% of the total, each representing 51% and 34% of the dementia, respectively. Other types of dementia accounting for 15% include ones caused by infectious disease and metabolic disease and the like. AD and vascular dementia are the most common types of dementia. However, there are no accurate methods for diagnosing the disease while the patients are alive and the current methods used are considered not reliable. Particularly in Korea, obtaining a brain sample from the patients after their death is particularly troublesome under the cultural environment of oriental thinking, and thus it makes the accurate pathological diagnosis almost impossible. Current clinical diagnosis of AD relies mainly on history taking and neuropsychology testing alternatively in conjunction with imaging technology such as MRI and PET. PiB-PET (Pittsburgh compound B-positron emission tomography), a method of imaging brains to detect the level of accumulation of Aβ in the brain, has been widely used for diagnosing AD and MCI, the cost of which, is however, high.

The accumulation of aggregates of Aβ in the brain, particularly the Aβ40(Aβ 1-40) and Aβ42(Aβ 1-42) is considered standard markers for AD. However, one unique method for testing these markers for diagnosing AD is to stain the plaque of fibrous Aβ aggregates in the postmortem brain by immunohistochemistry. Currently, there are no tests approved by FDA to pre-diagnosis of AD. A seeded multimerization method is used in which Aβ42 labelled with fluorescent materials or antibodies to Aβ42 are used. This is based on the assays described in Georganopoulou et al. PNAS, 2005, 102, 2273; Pitschke et al., Nature Medicine, 1998, 4(7), in which the amount of Aβ oligomers in the cerebrospinal fluid from the AD patient is found to be increased compared to that of the sample from a normal healthy person. Thus in such methods, the amount of the beta amyloid is measured in the cerebrospinal fluid of AD patients.

Aβs are not present as monomers in the blood, instead, they are present as aggregates of fibers which prevent the accurate detection thereof. For example, HSAs (Human Serum Albumin), a major protein component of blood, bind to Aβ forming a three dimensional structure therewith. As a result, Aβs are present concealed within the albumins, thus it is highly likely that the epitopes are not exposed making it difficult to be detected by anti-Aβ antibodies. Further, it is known that various proteases are present in the blood, which digest the proteins and thus prevent maintaining the stable concentration of the proteins.

Until present, there is not much research done with regards to the accurate determination of Aβ concentration. Thus there are needs to develop biological markers for more accurate and effective and early and diagnosis of AD and for evaluation of the potential therapeutic methods of treating AD. Particularly there are no simple diagnosis methods which are able to differentiate AD from Mild Cognitive Impairment (MCI), particularly in the blood.

Meanwhile, Korean Patent No. 10-1493935 discloses an imaging technology in which amyloid beta plaques are imaged using two photon fluorescent probes from isolated cells or tissues. And Korean Patent No. 10-1478609 discloses a diagnosing composition comprising curcumin derivatives or a pharmaceutically acceptable salt thereof. However, there are no disclosure as to quantifying Aβ in the plasma pretreated for diagnosis or prognosis of MCI and AD.

SUMMARY OF THE INVENTION

The present disclosure relates to a method of diagnosis or predicting a clinically reduced cognitive ability (or cognitive function) and a pathological Aβ accumulation in the brain by treating the blood (plasma) with a mixture of a protease inhibitor and a phosphatase inhibitor (MPP) and thus stabilizing Aβ42 and/or Aβ40 in the plasma and measuring the concentration thereof. Further, the present disclosure aims to provide a method for diagnosing and predicting the onset or development of Alzheimer's disease from the plasma concentrations of Aβ42 and/or Aβ40 measured by the above methods. Further, the present disclosure aims to provide a series of diagnostic systems to determine that the patients need a PET imaging through the prediction and diagnosis of a clinically reduced cognitive ability and a pathological Aβ accumulation in the brain based on the concentration of β42 and/or Aβ40 measured by the present methods To achieve the above object, the present invention provides a plasma pretreatment composition comprising a mixture of a protease inhibitor and a phosphatase inhibitor to reduce the concentration (distribution) standard deviation of plasma Aβ(amyloid beta).

In addition, the present invention provides a method for diagnosing and predicting cognitive dysfunction by detecting changes in the concentration and the concentration of Aβ in the plasma treated with the present plasma pretreatment composition and comparing the concentration with the average concentration determined in the plasma of normal controls.

The present invention also provides a method for measuring the concentration of Aβ in the plasma treated with the present plasma pretreatment composition and for predicting and diagnosing pathological accumulation of Aβ in the brain.

Also the present disclosure provide a system for diagnosing or predicting clinical and pathological Alzheimer disease comprising an information input unit to input a concentration of Aβ measured from a plasma sample of a subject pretreated with the present composition, a concentration of Hb measured from a blood sample of the subject and MMSE(z) value determined; a database unit in which an average concentration of Aβ measured in a plasma sample from a normal subject pretreated with the present composition is stored; and an information processing unit to perform a comparison analysis of comparing the input information with the information stored in the database and operating a regression analysis; and an information output unit to output results from the information processing unit.

Advantageous Effects

According to the present disclosure, clinical diagnosis of the subject in need thereof as MCI or AD, or pathological diagnosis of the subject in need thereof as to the accumulation of amyloid beta in the brain can be performed by the Aβ concentration determined in the plasma pretreated with the present MPP and/or TCEP. Also, the Aβ concentration determined by the present composition and methods can be used to determine the pathological accumulation of Aβ in the brain to predict the onset and progression into AD, which can replace the need for PET scan to determine the accumulation of Aβ.

BRIEF DESCRIPTION OF THE DRAWINGS

FIG. 1A is a comparison of Aβ prepared in vitro in monomer and fiber forms; and FIG. 1B is a graph showing the quantification of Aβ in monomer and fiber forms at the same concentration.

FIGS. 4A-4C are the results of showing the correlation of the brain Aβ plaque accumulation with the disease by comparison of the concentration of Aβ42 and Aβ40 in the plasma sample from the patients clinically diagnosed with cognitive impairment and treated with MPP with the PET imaging results from the corresponding patients.

DETAILED DESCRIPTION OF THE EMBODIMENTS

Figure 1A:
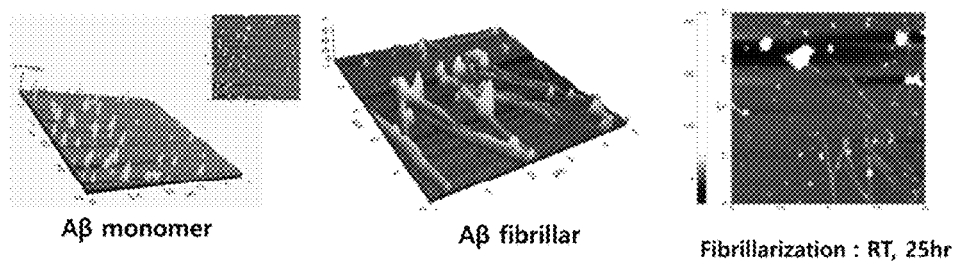
FIGS. 1A and 1B are the results of showing the measurement of the amount of Aβ prepared in vitro.

Now the present inventions are described in details hereinbelow. It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

In the present disclosure, the term "detection" or "measurement" refers to quantify the amount of the material of interest.

In the present disclosure, the term "Aβ40" may also be referred to as "Aβ 1-40".

In the present disclosure, the term "Aβ42" may also be referred to as "Aβ 1-42".

In the present disclosure, the term "normal control" may be interchangeably used with "normal healthy subject/person" and may further include PET positive or PET negative subjects, who are tested normal in a clinical cognitive diagnosis.

In the present disclosure, the term "composition for pretreating plasma (MPP)" refers to a mixture of protease inhibitors and phosphatase inhibitors, which may further comprise TCEP. The TCEP may be comprised in the present composition at the concentration of 3 mM. The present composition may comprise at least one protease inhibitors. Protease inhibitors which may be used in the present disclosure include ones conventionally used such as PMSF (phenylmethanesulfonylfluoride or phenylmethylsulfonyl fluoride). When two or more kinds of protease inhibitors are employed, they may be referred to PIC (protease inhibitor cocktail). According to the present disclosure, the protease inhibitors comprised in the present MPP compositions improve the stability of the protein(s) in the plasma, thus resulting in the stable and reliable determination of the concentration of Aβ.

In one aspect of the present disclosure, it is provided a composition for pretreating plasma comprising a mixture of protease inhibitors and phosphatase inhibitors. The present compositions are used to reduce the standard deviation of the concentration of Aβ measured in the plasma measured.

In one embodiment, the present composition for pretreating plasma comprises the protease inhibitors and phosphatase inhibitors at the ratio of 1:1 (v/v). Also, MPP may comprise PIC (Protease inhibitor cocktail):PMSF (Serine protease inhibitor):phosphatase inhibitor cocktail I: phosphatase inhibitor cocktail II at the ratio of 1:1:1:1(v/v). Also in other embodiment, the present composition for pretreating plasma may further comprise a TCEP.

In other aspect, the present disclosure provides a method of diagnosis or predicting cognitive impairment in a subject in need thereof, comprising treating a plasma sample obtained from the subject and a normal control with the present composition and quantifying the concentration of Aβ42 in the samples; comparing the average value determined in the subject sample with that determined in the normal control sample. In one embodiment, the cognitive impairment may include MCI (mild cognitive impairment) or AD (Alzheimer's disease). In one embodiment, when the concentration of Aβ42 in the subject plasma sample is decreased by more than 8.0% compared to the average concentration of Aβ42 in the normal control sample, the subject may be diagnosed or determined as having MIC with a specificity of at least 65%. In other embodiment, when the concentration of Aβ42 in the subject plasma sample is decreased by 8.0% to 11% compared to the average concentration of Aβ42 in the normal control sample, the subject may be diagnosed or determined as having MIC with a specificity of at least 65% and a sensitivity of at least 75%. In other embodiment, when the concentration of Aβ42 in the subject plasma sample is decreased by more than 9.0% compared to the average concentration of Aβ42 in the normal control sample, the subject may be diagnosed or determined as having AD with a specificity of at least 70%. In still other embodiment, when the concentration of Aβ42 in the subject plasma sample is decreased by 9.0% to 21% compared to the average concentration of Aβ42 in the normal control sample, the subject may be diagnosed or determined as having AD with a specificity of at least 70% and a sensitivity of at least 80%. In still other embodiment, when the concentration of Aβ42 in the subject plasma sample is decreased by more than 8.5% compared to the average concentration of Aβ42 in the normal control sample, the subject may be diagnosed or determined as having CI (MCI and AD) with a specificity of at least 65%. %. In still other embodiment, when the concentration of Aβ42 in the subject plasma sample is decreased by 8.5% to 10.0% compared to the average concentration of Aβ42 in the normal control sample, the subject may be diagnosed or determined as having as having CI (MCI and AD) with a specificity of at least 65% and a sensitivity of at least 75%. As described above, the present methods can be used to clinically determine that the subject in need thereof has problems in cognitive abilities.

In still other aspect, the present disclosure provides a method of determining the pathological accumulation of Aβ in the brain, the method comprising treating a plasma sample isolated from a subject in need thereof with the present pretreating composition and measuring a concentration of Aβ40 in the plasma; measuring a concentration of Hb (hemoglobin) from a blood sample isolated from the same subject; determining p value by applying the concentration of Aβ40, Hb, and MMSE score (Z) to the following logistic regression Formula 1 and 2; and comparing the p value above to the average p value of PET negative control sample.

$$\ln\left(\frac{Pi}{1-Pi}\right) = \beta_0 + \beta_1 x_{1,i} + \beta_2 x_{2,i} + \ldots + \beta_m x_{m,i} \quad \text{[Formula 1]}$$

($pi$: probability, $\beta_0$: constant, $\beta_m$: coefficient of variable)

$$\ln\left(\frac{Pi}{1-Pi}\right) = \beta_0 + \beta_1 x_{1,i} + \beta_2 x_{2,i} + \beta_3 x_{3,i}$$

(that is, $\beta_1$: coefficient of MPP-Aβ40,
$\beta 2$: coefficient of MMSE(Z) score;
$\beta 3$: coefficient of hemoglobin, x1: concentration of MPP-Aβ40, x2: value of MMSE(Z) score and x3: concentration of Hemoglobin), $$logit(p) = \ln\left(\frac{Pi}{1-Pi}\right) \quad \text{[Formula 2]}$$

$$P = \frac{1}{1+e^{-logit(p)}}.$$

In one embodiment, when the p value is increased at least by 190% compared to the average p value of PET negative control sample, it can be predicted that the brain of the subject is accumulated with Aβ with a specificity of at least 85%. In the present disclosure, the accumulation of Aβ in the brain may be confirmed by PiB-PET (Pittsburgh compound B-positron emission tomography) imaging. In one embodiment, it is predicted that the brain of the subject is accumulated with Aβ with a specificity of at least 85% and a sensitivity of at least 75% when the p value is increased by 190% to 230% compared to the average p value of PET negative sample. In the present disclosure, the accumulation of Aβ in the brain is indicated as PiB-PET positive (PiB-PET (+)).

In other aspect, a method of predicting or determining accumulation of Aβ in a brain of a subject in need thereof, comprising the steps of: 1) treating a plasma sample isolated from a subject in need thereof with the present pretreating composition and measuring a concentration of Aβ40 in the plasma; 2) treating a plasma sample isolated from the same subject in need thereof with the present pretreating composition further comprising TCEP and measuring a concentration of Aβ40 in the plasma; and 3) determining that the brain of the subject is accumulated with Aβ with a specificity of at least 65% and a sensitivity of at least 80% when the concentration of Aβ40 determined in step 2) is increased by more than 8.0 pg/ml compared to that of step 1). The particular amount of Aβ40 increased, such as increased by 9.24 pg/ml, can predict the accumulation of Aβ in the brain with a specificity of about 70% and a sensitivity of about 87%. Thus, it can be predicted that the probability of future progression into AD is high in those subjects as described above whom currently are considered normal in cognitive function.

The TCEP used in the present disclosure can separate Aβ bound to proteins such as albumin in plasma, and thus the detection of Aβ in plasma can be made more accurate. Also, in one embodiment of the present disclosure, compared with plasma treated with MPP containing protease inhibitor and phosphatase inhibitor alone, the concentration of Aβ40 in the plasma of normal subjects was increased when MPP containing TCEP was used. Thus by the method of the present invention, pathologically, it is possible to determine whether or not Aβ has accumulated in the brain.

In one aspect, the present invention relates to a method of determining or predicting both a cognitive impairment and an accumulation of Aβ in the brain by measuring the concentration of Aβ42 or Aβ40 in the plasma treated with a mixture of a protease inhibitor and a phosphatase inhibitor of the present disclosure.

In one embodiment of the present disclosure, the quantification (detection or measurement) of Aβ is measured by the Bioplex method and is significantly superior in sensitivity and specificity compared to other method such as ELISA (enzyme-linked immunosorbent assay).

In other aspect, the present disclosure relates to a method of predicting and/or monitoring the development of Alzheimer's disease in a subject in need thereof comprising the steps of treating a plasma sample obtained from the subject and a normal control with the present composition and quantifying the concentration of Aβ40 and/or Aβ42 in each sample; comparing the concentration of each sample to determine clinical cognitive impairment; and determining the accumulation of Aβ in the brain of the subject by comparing p value to the average p value of PET negative control sample wherein the p value is determined by applying the concentration of Aβ40, the concentration of hemoglobin determined in the blood from the same subject and MMSE(Z) score to the mathematical Formula 1 and 2 above.

In other aspect, the present disclosure relates to a method to provide information needed for monitoring the progression of MCI (Mild Cognitive Impairment) to AD (Alzheimer's disease). By the present methods, it is possible to differentiate MCI and AD, and differentiate PiB-PET negative and positive. Thus, in addition to a simple clinical diagnosis of decreased cognitive function, it is also possible to diagnose actual pathological progression of the disease.

In other aspect, the present disclosure relates to a system for predicting and diagnosis of clinical and pathological Alzheimer disease comprising: 1) an information input unit to input a concentration of Aβ40 or Aβ 42 measured from the plasma sample of a subject in need of thereof in which the plasma is pretreated with the present composition, a concentration of Hb measured from a blood sample of the subject and MMSE(z) value determined; 2) a database unit in which an average concentration of Aβ measured in a plasma sample from a normal healthy subject in which the sample is pretreated with the present composition, and an average p value determined in a PET negative sample are stored; and 3) an information processing unit to perform an comparison analysis of comparing the input information of 1) with the information stored in 2) and perform the operations of a logistic regression analysis of mathematical Formula 1 and Formula 2; and an information output unit for outputting a result calculated by the information processing unit. In one embodiment, the present disclosure relates to a system for predicting and diagnosis of clinical and pathological Alzheimer disease comprising: 1) a step of inputting the concentration of Aβ40 measured in a plasma sample isolated from a subject in need thereof into an information input unit; 2) a step of further inputting the concentration of hemoglobin measured from a blood sample from the same subject, and the MMSE(z) measurement value into the information input unit, when the concentration of Aβ40 measured in a plasma sample isolated from a subject in need thereof and input into the information input unit, is decreased by more than 8.5% compared to the average concentration of Aβ40 measured from normal healthy subjects and stored in the database unit; performing the logistic regression analysis of Formula (1) and the calculation of Formula (2) using the input information of the steps 1) and 2) and the information stored in the database to instruct the information processing unit to derive a P value; and 4) based on the logistic regression analysis, when the p value derived from the subject is increased by at least 190.0% compared to the average p value of the PET negative control group stored in the database, it is predicted that the subject is clinically diagnosed as cognitive dysfunction and is pathologically accumulated with Aβ in the brain.

Figure 9:
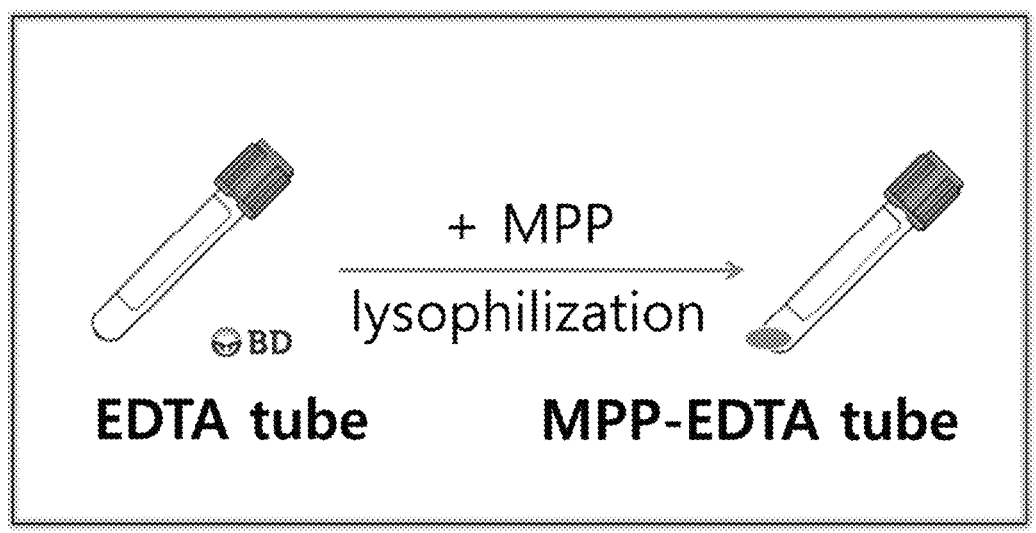
FIG. 9 shows an exemplary device for collecting blood comprising anti-coagulants of the blood and the present composition for pretreating plasma sample.
Figure 10:
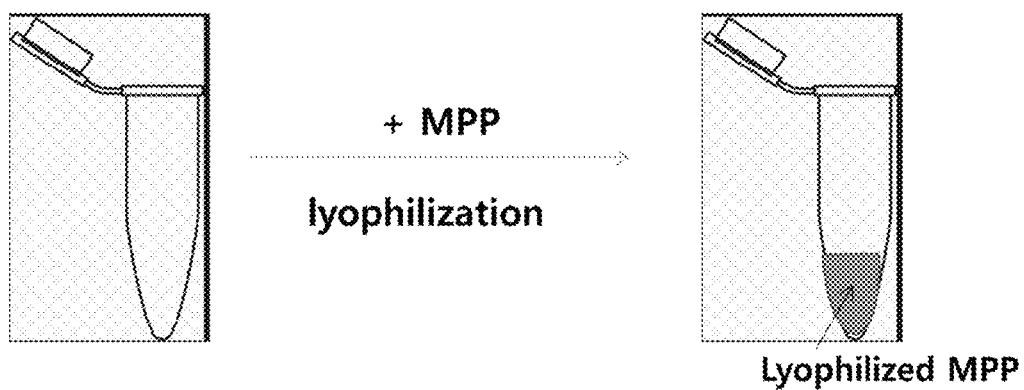
FIG. 10 shows an exemplary device for collecting plasma for storing the plasma separated from the blood collected from the patients.
Figure 11:
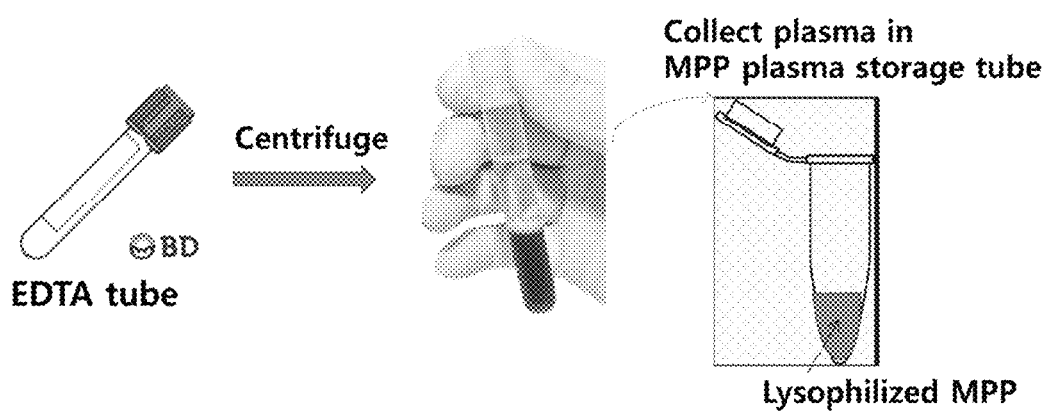
FIG. 11 shows an exemplary process for collecting plasma using the exemplary device for collecting plasma comprising the present composition for pretreating plasma sample.

In other aspect, the present disclosure provides a blood collecting apparatus comprising the plasma pretreatment composition of the present disclosure (see FIG. 9). In one embodiment, the blood collecting apparatus may be an apparatus, for example a blood collection tube, an eppendorf tube or a kit, which further comprises a blood coagulation inhibitor, wherein the blood coagulation inhibitor may include any materials preventing the coagulation such as EDTA. In another aspect, the present disclosure provides a plasma collection device comprising the plasma pretreatment composition of the present invention (see FIG. 10). In one embodiment, the plasma collection device can be used to collect and store only the plasma sample isolated from the whole blood of the subject in the blood collection device (see FIG. 11). In one embodiment, the present plasma pretreatment composition of the present disclosure may be lyophilized and included in the device, and about 340 μl of the present plasma pretreatment composition per about ~8.5 ml blood (whole blood) or 3 to 4 ml plasma can be included. The present plasma pretreatment compositions may include protease inhibitors and phosphatase inhibitors, including, for example, AEBSF 26 mM, Aprotinin 20 uM, Bestatin 1 mM, E-64 0.35 mM, Leupeptin 0.5 mM, Pepstatin A 0.375 mM, (−)-p-Bromotetramisole oxalate 0.625 mM, Cantharidin 125 uM, Microcystin LR 125 nM, Imidazole 50 mM, Sodium Fluoride 25 mM, Sodium Molybdate 28.75 mM, Sodium orthovanadate 25 mM, Tartrate Dihydrate 100 mM and PMSF (Phenylmethanesulfonylfluoride) 25 mM. The blood collection device or apparatus of the present disclosure may be stored at 2-8° C. after the blood or plasma collection.

The present disclosure is further explained in more detail with reference to the following examples. These examples, however, should not be interpreted as limiting the scope of the present invention in any manner.

EXAMPLES

Figure 1B:
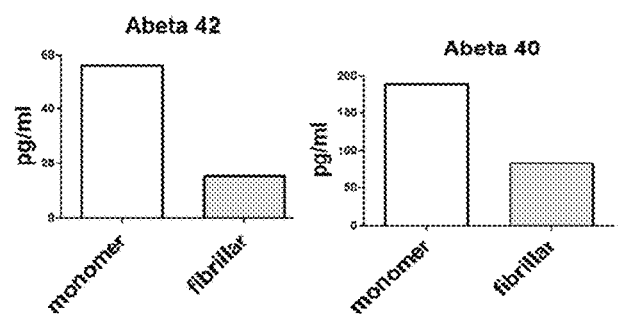

<Example 1> Comparison of the Detectability of Aβ Depending on the Types of its Forms: Monomeric and Aggregated Fibrillary Form To determine how accurately the actual concentration of the Aβ depending on its monomer and fibrillar form in vitro, the known amount of each of Aβ forms prepared as described below was compared to the concentration measured by the conventional methods as described below. Specifically, the Aβ peptides were purchased from Bachem Americas, Inc. (Torrance, Calif., USA) and prepared in accordance with the manufacturer's guidelines. To prepare Aβ monomers, Aβ peptides were dissolved in DMSO and lyophilized by Speed-vac (Thermo savant, Bartlesville, USA). The fibrillar Ms were prepared by the incubation of Aβ monomers for 24 hours at room temperature. Protease inhibitor cocktail, serine protease inhibitor (PMSF), and human serum albumin (HSA) were purchased from Sigma Aldrich (CA, USA), Phosphatase inhibitor cocktail I (Lot #D1151) was purchased from A.G. Scientific Inc. the monomeric Aβ and fibrillar Aβ were prepared at the same concentration. Then the concentration the monomeric and fibrillar form prepared at the same concentration as above were determined by using INNO-BIA plasma Aβ forms kit (Innogenetics, Gent, Belgium) in accordance with manufacturer's directions and X-map technology (Bioplex 200 systems; Bio-rad, Hercules, Calif., USA). As a result, it was found that the Aβ in both forms is detected at a concentration lower than their respective actual concentrations; particularly it is significantly lower with the fibrillar form compared to the monomeric form (FIGS. 1A and 1B). This indicates that Aβ monomer form can be detected more accurately than the aggregated fibrillar form and there needs an improvement for measuring the aggregated form.

Figures 2A, 2B:
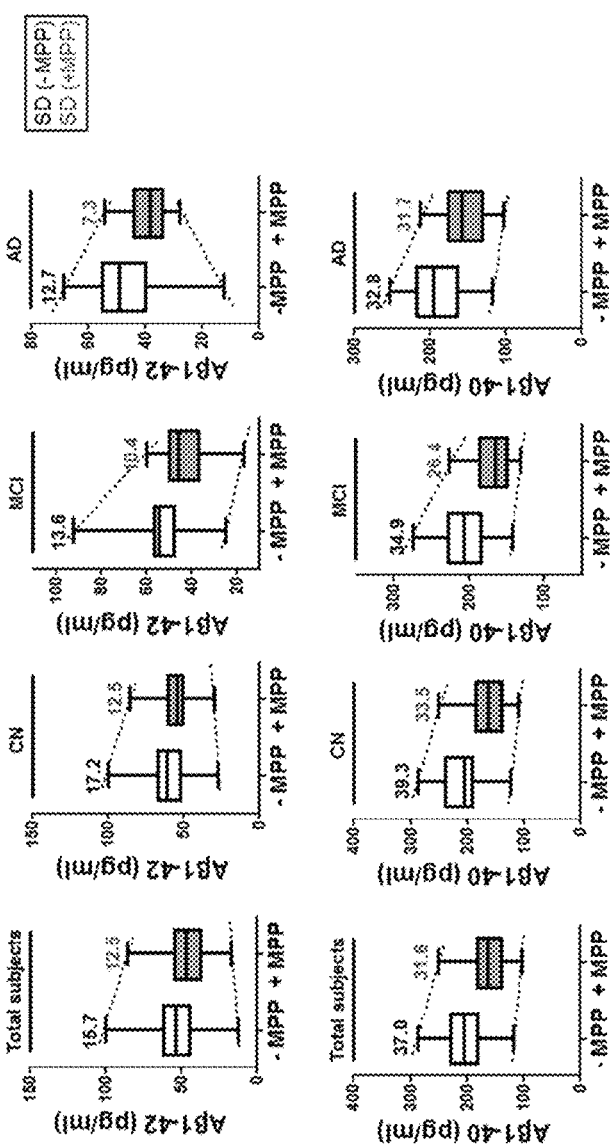
FIGS. 2A and 2B are the results showing the effect of MPP treatment of the plasma on the quantification of Aβ in the plasma sample.

<Example 2> The Differentiation of Clinical Cognitive Impaired Subjects from Normal Subject by Measuring Aβ Concentration in the Plasma Treated with the Present Composition <2-1> Decrease in the Standard Deviation of Concentration of Plasma Aβ42 and Aβ40 by the Present MPP Treatment To determine simultaneously the concentrations of plasma Aβ42 and Aβ40, we used the INNO-BIA plasma Aβ forms kit (Innogenetics, Gent, Belgium) in accordance with manufacturer's directions and performed X-map technology (Bioplex 200 systems; Bio-rad, Hercules, Calif., USA). Plasma samples were obtained from the subjects having characteristics in Table 1. The blood samples were obtained via venipuncture after an overnight fast and collected in K2 EDTA tubes (BD Vacutainer Systems, Plymouth, UK). The samples were stabilized and centrifuged at 700×g for 5 min at room temperature, to obtain plasma supernatants in 15 ml centrifuge tubes (SPL Life Sciences Co., Gyeonggi-do, Korea). To obtain samples with high purity, the plasma supernatants were further centrifuged under the same condition, and the collected pure plasma supernatants were aliquoted and immediately stored at −80° C. Mixture of Protease inhibitors and phosphatase inhibitors (MPP) was composed of protease inhibitor cocktail (PI): phenylmethanesulfonylfluoride (PMSF, a serine protease inhibitor; Sigma Aldrich, Calif., USA): phosphatase inhibitor cocktail I: phosphatase inhibitor cocktail II (PPI I and II; A. G. Scientific, Inc., CA, USA) at the ratio of 1:1:1:1(v/v). That is, the protease inhibitor and phosphate inhibitor were mixed at the ratio of 1:1(v/v). To measure the Aβ concentration in the plasma after treating the plasma with MPP, the MPP was diluted in the plasma diluent buffer at ¹⁄₂₅ to prepared MPP-treated diluent buffer, the plasma collected was then diluted 3-fold in the MPP-treated plasma diluent buffer or MPP non-treated plasma diluent buffer (the plasma diluent comprising MPP: human plasma sample=2:1) and incubated for 30 min at room temperature. Consequently, the levels of plasma Aβ were measured by X-map technology (Bioplex 200 systems; Bio-rad, Hercules, Calif., USA), and the standard deviation values were obtained from the MPP treated and MPP non-treated samples (FIGS. 2A and 2B).

TABLE 1

Baseline characteristics of subjects in the study.

| Characteristics | Normal controls (n = 23) | MCI (n = 15) | AD (n = 16) | P-value |
|---|---|---|---|---|
| Sex, M/F | 7/16 | 3/12 | 4/12 | — |
| Age, years, mean ± SE | 71.9 ± 1.1 | 74.9 ± 1.3 | 69.8 ± 2.1 | 0.2226 |
| Education, mean ± SE | 12.5 ± 1.1 | 8.3 ± 1.1 | 9.7 ± 1.2 | 0.0173 |
| MMSE score, mean ± SE | 27.0 ± 0.4 | 22.7 ± 1.0 | 16.4 ± 0.7 | <0.0001 |

TABLE 1-continued

Baseline characteristics of subjects in the study.

| Characteristics | Normal controls (n = 23) | MCI (n = 15) | AD (n = 16) | P-value |
|---|---|---|---|---|
| CDR (n) | 0 (23) | 0.5 (15) | 0.5 (5), 1 (11) | <0.0001 |
| ApoE types (n) | E2/E3 (3) | E2/E3 (3) | E2/E3 (0) | — |
|  | E2/E4 (2) | E3/E3 (6) | E3/E3 (7) |  |
|  | E3/E3 (14) | E3/E4 (4) | E3/E4 (7) |  |
|  | E3/E4 (4) | E4/E4 (2) | E4/E4 (2) |  |
| PiB-PET−/+, n | 17/6 | 9/6 | —/16 | — |

Abbreviations; CN, cognitively normal subjects; MCI, mild cognitive impairment subjects; AD, Alzheimer's Disease patients; MMSE z-score, revised Mini-Mental State Examination considering age, sex and education; CDR, Clinical Dementia Rating; SE, Standard Error; n, number of subjects
CN: Cognitively Normal
MCI: Mild Cognitive Impairment subjects
AD: Alzheimer's disease
MMSE z-score: Mini-Mental State Examination z-score, one part of the assessment process for dementia, revised value of MMSE score (controlled for age, sex, and education level).
CDR: Clinical Dementia Rating
SD: Standard deviation
NA: Not Available
n: number of subjects As a result, it was found that the standard deviation (SD) of Aβ1-42 and Aβ1-40 concentrations measured in the plasma sample pre-treated with the present MPP (FIGS. 2A and 2B) were decreased in all the subject tested regardless of the types classified (CN, MCI, AD) compared to the non-treated group. In other words, this result shows that the reproducibility and reliability of Aβ detection (more especially in Aβ40) were significantly increased by the treatment of the present MPP.

<2-2> Analysis of the Correlation Between the Concentrations of Aβ Measured in Plasma Sample Treated with the Present MPP and the Results of Clinical Testing of Cognitive Impairment The data of detected Aβ42 and Aβ40 concentration of Example 2-1 were collected, and statistical analysis was performed using GraphPad Prizm 5 (GraphPad Software, San Diego, Calif., USA) and Medcalc (Medcalc Software, Ostend, Belgium). All data are presented as mean±standard error (SEM). An unpaired Student's t-test was also used to assess quantitative differences between Aβ concentration and PiB-PET positive and negative groups. To confirm the performance efficiency to differentiate among three groups, multifactorial analyses of variance (ANOVA) followed by Tukey's multiple-comparisons tests (GraphPad Prizm 5) were performed. To evaluate the performance of pre-screening tests for discrimination of participant groups, we conducted stepwise logistic regression analysis and ROC(Receiver Operating Characteristics) curve analysis using MedCalc. AUC (Area under the curve) and ROC curve were generated based on the concentration of Aβ determined as described above by Wilcoxon method.

Figure 3A:
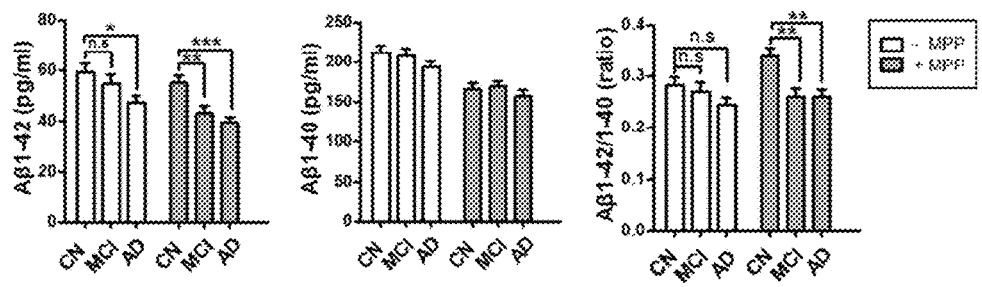
FIGS. 3A-3C are the results of verifying the correlation between [concentration of Aβ] and [normal person and MCI], [normal person and AD] and [normal person and CI (MCI and AD)] by determining the concentration of Aβ42 and Aβ40 in the plasma treated with MPP and MMSE score (Z).
Figure 3B:
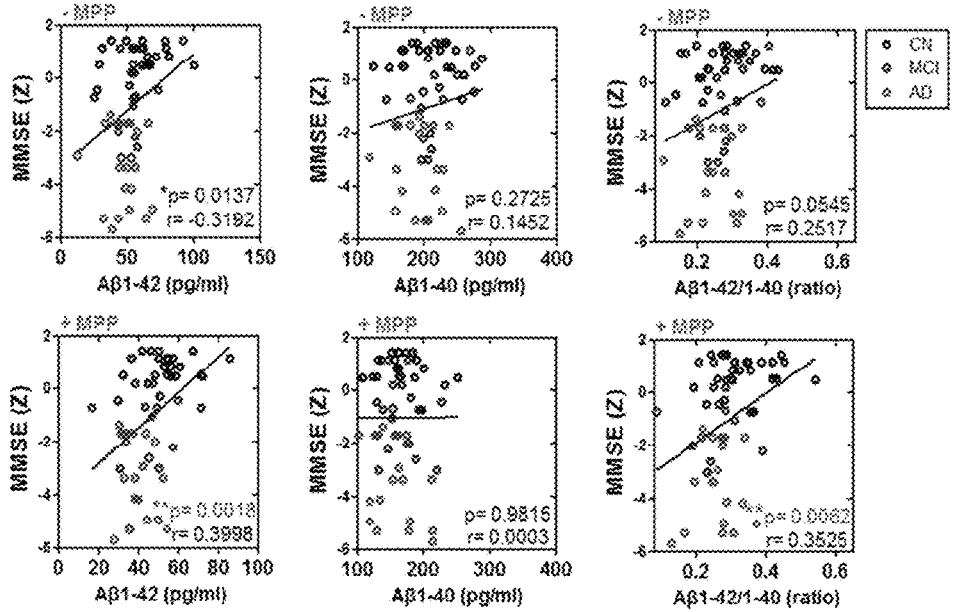
Figure 3C:
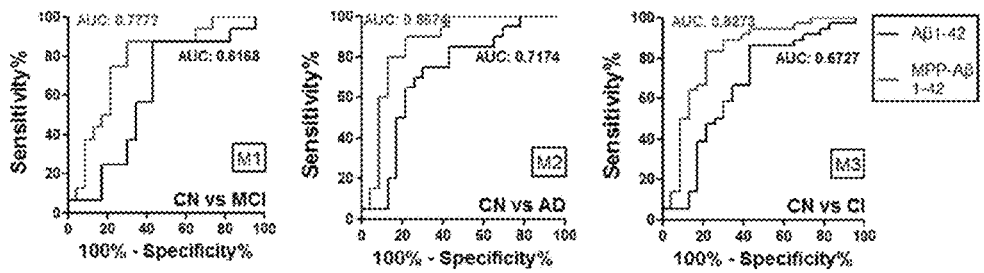

We assessed the ability of MPP treated Aβ to discriminate between the CN (control normal) group and each patient group. First, we performed a subsequent logistic regression by applying Aβ1-42 concentration measured with correction parameters (gender, age and education level), and an ROC curve analysis. As a result, when we used MPP-Aβ1-42, the model AUC values were fairly higher in all the groups of comparison (CN vs MCI, CN vs AD, and CN vs CI (cognitively impaired patients, MCI and AD)) compared to the MPP non-treated Aβ1-42 as follows: CN vs MCI, AUC 77.7% with a sensitivity (to ability to determine the diseased person as diseased) of 87.5% and specificity (the ability to determine the non-diseased person as not diseased) of 69.6%; CN vs AD, AUC 86.7% with sensitivity 90.0% and specificity 78.3%; CN vs CI, AUC 82.7% with sensitivity 83.3% and specificity 78.3%) (FIGS. 3A-3C and Table 2). It suggests that our model provides the role of MPP-Aβ1-42 as an indicator or marker for clinical diagnosis as to cognitive ability. Furthermore, the criterion results by the logistic regression show that the subjects with low MPP-Aβ42 measured in the plasma sample treated with the present MPP can be classified as MCI (50.24 pg/ml or lower), as AD (49.90 pg/ml or lower), or CI (49.90 pg/ml or lower) (FIGS. 3A-3C and Table 2).

TABLE 3-continued

| Criterion | Sensitivity | 95% CI | Specificity | 95% CI | +LR | −LR |
|---|---|---|---|---|---|---|
| ≤59.68 | 100.00 | 79.4-100.0 | 26.09 | 10.2-48.4 | 1.35 | 0.00 |
| ≤85.75 | 100.00 | 79.4-100.0 | 0.00 | 0.0-14.8 | 1.00 | |

TABLE 2

Diagnostic value of PIC-Aβ and other biological factors for discrimination between normal controls and cognitively impaired patients or PiB-PET negative subjects and positive subjects.

| Discrimination | Parameters | AUC (%) | Sensitivity (%) | Specificity (%) | Criterion | P-value (Coefficients) | P-value (Area = 0.5) | Increase in AUC (%) after PIC |
|---|---|---|---|---|---|---|---|---|
| (A) Discrimination ability of single markers (stepwise procedure not available) | | | | | | | | |
| CN vs MCI | MPP-Aβ 1-42 | 77.7% | 87.5% | 69.6% | ≤50.24 pg/ml | — | 0.0004 | 16.0% |
| CN vs AD | PIC-Aβ 1-42 | 86.7% | 90.0% | 78.3% | ≤49.90 pg/ml | — | <0.0001 | 15.0% |
| CN vs CI (CI, MCI + AD) | PIC-Aβ 1-42 | 82.7% | 83.3% | 78.3% | ≤49.90 pg/ml | — | <0.0001 | 15.5% |

AUC: Area under curve
CI: Cognitive Impaired subjects (that is, including MCI and AD)

<2-2-1> The Discrimination of MCI from CN

On the basis of the data presented in <Example 2-2>, the tolerance interval of the criterion (±15% of the sensitivity and specificity on the cut off criterion) is listed in table 3 and table 4 (orange: tolerance interval of criterion; red: criterion value; table 4 shows the cut-off criterion of table 3). Specifically since it was found that the average MPP-Aβ42 concentration of CN is 55.1 pg/ml and the optimal reliable cut off range (based on the tolerance interval of criterion) is 49.20 pg/ml to 50.24 pg/ml, the subjects who have reduced plasma Aβ by at least 8.9% to 10.7% compared with the average plasma Aβ of CN can be diagnosed as MCI. For example, it can be interpreted that the subject with the Aβ42 concentration reduced by below 8.9% compared to the average concentration Aβ42 of normal control are not diagnosed as MCI, but when the concentration is reduced by more than 10.7%, the subject is diagnosed as MCI, while it is more reliable that the reduction by 8.9% to 10.7% compared to the average concentration of normal control is used as a value to diagnose MCI.

TABLE 3

| Criterion | Sensitivity | 95% CI | Specificity | 95% CI | +LR | −LR |
|---|---|---|---|---|---|---|
| <16.63 | 0.00 | 0.0-20.6 | 100.00 | 85.2-100.0 | | 1.00 |
| ≤16.63 | 6.25 | 0.2-30.2 | 100.00 | 85.2-100.0 | | 0.94 |
| ≤29.74 | 6.25 | 0.2-30.2 | 95.65 | 78.1-99.9 | 1.44 | 0.98 |
| ≤30.71 | 12.50 | 1.6-38.3 | 95.65 | 78.1-99.9 | 2.88 | 0.91 |
| ≤32.06 | 12.50 | 1.6-38.3 | 91.30 | 72.0-98.9 | 1.44 | 0.96 |
| ≤38.21 | 37.50 | 15.2-64.6 | 91.30 | 72.0-98.9 | 4.31 | 0.68 |
| ≤41.56 | 37.50 | 15.2-64.6 | 86.96 | 66.4-97.2 | 2.87 | 0.72 |
| ≤43.41 | 43.75 | 19.8-70.1 | 86.96 | 66.4-97.2 | 3.35 | 0.65 |
| ≤44.54 | 43.75 | 19.8-70.1 | 82.61 | 61.2-95.0 | 2.52 | 0.68 |
| ≤45.01 | 50.00 | 24.7-75.3 | 82.61 | 61.2-95.0 | 2.87 | 0.61 |
| ≤46.41 | 50.00 | 24.7-75.3 | 78.26 | 56.3-92.5 | 2.3 | 0.64 |
| ≤49.2 | 75.00 | 47.6-92.7 | 78.26 | 56.3-92.5 | 3.45 | 0.32 |
| ≤50.08 | 75.00 | 47.6-92.7 | 69.57 | 47.1-86.8 | 2.46 | 0.36 |
| ≤50.24 | 87.50 | 61.7-98.4 | 69.57 | 47.1-86.8 | 2.87 | 0.18 |
| ≤56.24 | 87.50 | 61.7-98.4 | 34.78 | 16.4-57.3 | 1.34 | 0.36 |
| ≤57.12 | 93.75 | 69.8-99.8 | 34.78 | 16.4-57.3 | 1.44 | 0.18 |
| ≤58.65 | 93.75 | 69.8-99.8 | 26.09 | 10.2-48.4 | 1.27 | 0.24 |

TABLE 4

| Criterion | Sensitivity | 95% CI | Specificity | 95% CI | +LR | −LR |
|---|---|---|---|---|---|---|
| ≤49.2 | 75.00 | 47.6-92.7 | 78.26 | 56.3-92.5 | 3.45 | 0.32 |
| ≤50.08 | 75.00 | 47.6-92.7 | 69.57 | 47.1-86.8 | 2.46 | 0.36 |
| ≤50.24 | 87.50 | 61.7-98.4 | 69.57 | 47.1-86.8 | 2.87 | 0.18 |

<2-2-2> The Discrimination of AD from CN

On the basis of the data presented in <Example 2-2>, the tolerance interval of the criterion (±15% of the sensitivity and specificity on the cut off criterion) is listed in table 5 and table 6 (orange, tolerance interval of criterion; red, criterion value; table 6 shows the cut-off criterion of table 5). Specifically since it was found the average MPP-Aβ concentration of CN is 55.1 pg/ml and the optimal reliable cut off range (based on the tolerance interval of criterion) is 44.90 pg/ml to 49.9 pg/ml, the subjects who have reduced plasma Aβ by at least 9.5% to 20.1% compared with the average plasma Aβ42 concentration of CN can be diagnosed as AD. For example, it can be interpreted that the subject with the reduction of Aβ by below 9.5% compared to the average concentration Aβ42 of normal control are not diagnosed as AD, but when the concentration is reduced by at least 20.1%, the subject is diagnosed as AD, while it is more reliable that the reduction by 9.5% to 20.1% compared to the average concentration of normal control is used as a value to diagnose AD.

TABLE 5

| Criterion | Sensitivity | 95% CI | Specificity | 95% CI | +LR | −LR |
|---|---|---|---|---|---|---|
| <27.8 | 0.00 | 0.0-16.8 | 100.00 | 85.2-100.0 | | 1.00 |
| ≤27.8 | 5.00 | 0.1-24.9 | 100.00 | 85.2-100.0 | | 0.95 |
| ≤29.74 | 5.00 | 0.1-24.9 | 95.65 | 78.1-99.9 | 1.15 | 0.99 |
| ≤31.04 | 15.00 | 3.2-37.9 | 95.65 | 78.1-99.9 | 3.45 | 0.89 |
| ≤32.06 | 15.00 | 3.2-37.9 | 91.30 | 72.0-98.9 | 1.72 | 0.93 |
| ≤39.64 | 60.00 | 36.1-80.9 | 91.30 | 72.0-98.9 | 6.90 | 0.44 |
| ≤41.56 | 60.00 | 36.1-80.9 | 86.96 | 66.4-97.2 | 4.60 | 0.46 |

TABLE 5-continued

| Criterion | Sensitivity | 95% CI | Specificity | 95% CI | +LR | −LR |
|---|---|---|---|---|---|---|
| ≤44.04 | 80.00 | 56.3-94.3 | 86.96 | 66.4-97.2 | 6.13 | 0.23 |
| ≤46.41 | 80.00 | 56.3-94.3 | 78.26 | 56.3-92.5 | 3.68 | 0.26 |
| ≤49.9 | 90.00 | 68.3-98.8 | 78.26 | 56.3-92.5 | 4.14 | 0.13 |
| ≤50.7 | 90.00 | 68.3-98.8 | 60.87 | 38.5-80.3 | 2.30 | 0.16 |
| ≤52.03 | 95.00 | 75.1-99.9 | 60.87 | 38.5-80.3 | 2.43 | 0.082 |
| ≤52.77 | 95.00 | 75.1-99.9 | 56.52 | 34.5-76.8 | 2.18 | 0.088 |
| ≤54.06 | 100.00 | 83.2-100.0 | 56.52 | 34.5-76.8 | 2.30 | 0.00 |
| ≤85.75 | 100.00 | 83.2-100.0 | 0.00 | 0.0-14.8 | 1.00 | |

TABLE 6

| Criterion | Sensitivity | 95% CI | Specificity | 95% CI | +LR | −LR |
|---|---|---|---|---|---|---|
| ≤44.04 | 80.00 | 56.3-94.3 | 86.96 | 66.4-97.2 | 6.13 | 0.23 |
| ≤46.41 | 80.00 | 56.3-94.3 | 78.26 | 56.3-92.5 | 3.68 | 0.26 |
| ≤49.9 | 90.00 | 68.3-98.8 | 78.26 | 56.3-92.5 | 4.14 | 0.13 |

<2-2-3> The Discrimination of CI (MCI+AD) from CN

On the basis of the data presented in <Example 2-2>, the tolerance interval of the criterion (±15% of the sensitivity and specificity on the cut off criterion) is listed in table 7 and table 8 (orange, tolerance interval of criterion; red, criterion value; table 8 shows the cut-off criterion of table 7). Specifically since it was found that the average MPP-Aβ42 concentration of CN is 55.1 pg/ml and the reliable optimal cut off range (based on tolerance interval of criterion) is 44.90 pg/ml to 50.24 pg/ml, the subjects who have reduced plasma Aβ by at least 8.9% to 9.5% compared with the average plasma Aβ42 of CN can be diagnosed as CI. For example, it can be interpreted that the subjects with the reduction of Aβ by below 8.9% compared to the average concentration Aβ42 of normal control are not diagnosed as CI, but when the concentration is reduced by at least 9.5%, the subject is diagnosed as CI, while it is more reliable that the reduction by 8.9% to 9.5% compared to the average concentration of normal control is used as a value to diagnose CI.

TABLE 7

| Criterion | Sensitivity | 95% CI | Specificity | 95% CI | +LR | −LR |
|---|---|---|---|---|---|---|
| <16.63 | 0.00 | 0.0-9.7 | 100.00 | 85.2-100.0 | | 1.00 |
| ≤27.8 | 5.56 | 0.7-18.7 | 100.00 | 85.2-100.0 | | 0.94 |
| ≤29.74 | 5.56 | 0.7-18.7 | 95.65 | 78.1-99.9 | 1.28 | 0.99 |
| ≤31.04 | 13.89 | 4.7-29.5 | 95.65 | 78.1-99.9 | 3.19 | 0.90 |
| ≤32.06 | 13.89 | 4.7-29.5 | 91.30 | 72.0-98.9 | 1.60 | 0.94 |
| ≤39.64 | 50.00 | 32.9-67.1 | 91.30 | 72.0-98.9 | 5.75 | 0.55 |
| ≤41.56 | 50.00 | 32.9-67.1 | 86.96 | 66.4-97.2 | 3.83 | 0.58 |
| ≤44.04 | 63.89 | 46.2-79.2 | 86.96 | 66.4-97.2 | 4.90 | 0.42 |
| ≤44.54 | 63.89 | 46.2-79.2 | 82.61 | 61.2-95.0 | 3.67 | 0.44 |
| ≤45.01 | 66.67 | 49.0-81.4 | 82.61 | 61.2-95.0 | 3.83 | 0.40 |
| ≤46.41 | 66.67 | 49.0-81.4 | 78.26 | 56.3-92.5 | 3.07 | 0.43 |
| ≤49.9 | 83.33 | 67.2-93.6 | 78.26 | 56.3-92.5 | 3.83 | 0.21 |
| ≤50.08 | 83.33 | 67.2-93.6 | 69.57 | 47.1-86.8 | 2.74 | 0.24 |
| ≤50.24 | 88.89 | 73.9-96.9 | 69.57 | 47.1-86.8 | 2.92 | 0.16 |
| ≤50.7 | 88.89 | 73.9-96.9 | 60.87 | 38.5-80.3 | 2.27 | 0.18 |
| ≤52.03 | 91.67 | 77.5-99.3 | 60.87 | 38.5-80.3 | 2.34 | 0.14 |
| ≤52.77 | 91.67 | 77.5-99.3 | 56.52 | 34.5-76.8 | 2.11 | 0.15 |
| ≤54.06 | 94.44 | 81.3-100.0 | 56.52 | 34.5-76.8 | 2.17 | 0.098 |
| ≤56.24 | 94.44 | 81.3-100.0 | 34.78 | 16.4-57.3 | 1.45 | 0.16 |
| ≤57.12 | 97.22 | 85.5-99.9 | 34.78 | 16.4-57.3 | 1.49 | 0.080 |
| ≤58.65 | 97.22 | 85.5-99.9 | 26.09 | 10.2-48.4 | 1.32 | 0.11 |
| ≤59.68 | 100.00 | 90.3-100.0 | 26.09 | 10.2-48.4 | 1.35 | 0.00 |
| ≤85.75 | 100.00 | 90.3-100.0 | 0.00 | 0.0-14.8 | 1.00 | |

TABLE 8

| Criterion | Sensitivity | 95% CI | Specificity | 95% CI | +LR | −LR |
|---|---|---|---|---|---|---|
| ≤49.9 | 80.00 | 67.2-93.6 | 78.26 | 56.3-92.5 | 3.83 | 0.21 |
| ≤50.08 | 80.00 | 67.2-93.6 | 69.57 | 47.1-86.8 | 2.74 | 0.24 |
| ≤50.24 | 88.89 | 73.9-96.9 | 69.57 | 47.1-86.8 | 2.92 | 0.16 |

<Example 3> Identification of the Association of Aβ Concentration Measured in the MPP-Treated Plasma with Pathological Aβ Accumulation in Patients <3-1> Identification of the Correlation Between MPP-Aβ42 or MPP-Aβ40 Measured in the MPP-Treated Plasma and the Accumulation of Amyloid Plaques in the Brain To evaluate the relationship between the MPP-treated plasma Aβ concentration and the brain Aβ deposition in the participants, we compared the Aβ concentration in plasma measured in the plasma treated with the present MPP with the global cortical SUVR (Standardized Uptake Value Ratio) data. Briefly, statistical analysis was performed as described in <Example 2> and we conducted logistic regression analysis with Medcalc and measured the relationship between dependent variables (PiB-PET positive subjects or PiB-PET negative subjects) and independent variables (MPP-treated plasma Aβ concentration).

As a result, there were negative correlations between Aβ40 concentration in the MPP treated plasma and the global cortical SUVR, in all regions (global cortical, p=0.0432; lateral parietal, p=0.0347; lateral temporal, p=0.0226; PC-PRC, p=0.0453) (FIGS. 4A-4C).

<3-2> Identification of the Correlation Between Aβ Concentration in the MPP Treated Plasma and the Accumulation of Amyloid Plaques in the Brain We next tried to differentiate PiB-PET positive vs. PiB-PET negative by using the Aβ40 concentration measured in the plasma treated with the present MPP. For this, we compared the MPP-Aβ40 concentrations between the PiB-PET positive subjects and the PiB-PET negative subjects by unpaired t-tests and generated the ROC curves, as described in <Example 3-1>. Briefly, we conducted logistic regression analysis with Medcalc using independent variables ('MPP-Aβ40' or 'MPP-Aβ40, MMSE z-score' or 'MPP-Aβ40, MMSE z-score, Hemoglobin in whole blood') and formula 1. Also, we calculated p-value (formula 2) using the pi values from formula 1. Finally, we generated the ROC curves by using the calculated p-values and determined the cut-off values (criterion) therefrom.

$$\ln\left(\frac{Pi}{1-Pi}\right) = \beta_0 + \beta_1 x_{1,i} + \beta_2 x_{2,i} + \ldots + \beta_m x_{m,i} \quad \text{[Formula 1]}$$

($pi$: probability, $\beta_n$: coefficient, $\beta_0$: constant) or $$\ln\left(\frac{Pi}{1-Pi}\right) = \beta_0 + \beta_1 x_{1,i} + \beta_2 x_{2,i} + \beta_3 x_{3,i}$$

($\beta_0$: constant, $\beta_1$: coefficient of MPP-Aβ40,
$\beta_2$: coefficient of MMSE(Z),
$\beta_3$: coefficient of Hemoglobin,
$\beta_1$: coefficient of MPP-Aβ40, $\beta_2$: coefficient
of MMSE(Z), $\beta_3$: coefficient of Hemoglobin,
$x_1$: MPP-Aβ40 value, $x_2$: MMSE(Z) score,
and $x_3$: Hemoglobin value), -continued $$logit(p) = \ln\left(\frac{Pi}{1-Pi}\right)$$ [Formula 2]

$$P = \frac{1}{1+e^{-logit(p)}}$$

Figure 5A:
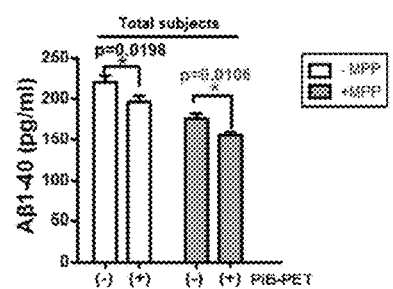
FIGS. 5A and 5B are the results verifying the correlation between the positive or negative PiB-PET scan results and the concentration of Aβ40 in the plasma treated with MPP or other factors (MMSE Z-score and concentration of hemoglobin in the blood).
Figure 5B:
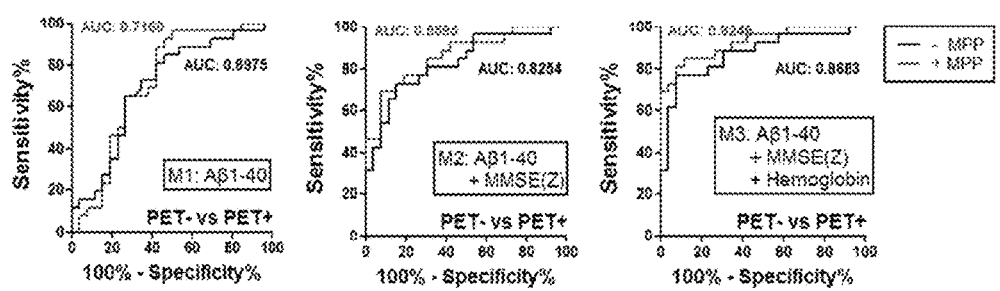

Consequently, the AUC values of 'MPP-Aβ40', 'MPP-Aβ40+MMSE(z)', and 'MPP-Aβ40+MMSE(z)+Hb' were increased in sequence and the discrimination power was highest in 'MPP-Aβ40+MMSE(z)+Hb' model (FIGS. 5A and 5B and Table 9). Also, by using the cut-off criterions from the logistic regression analysis, the PiB-PET positive from PiB-PET negative (Table 9) can be distinguished. Thus, the subjects who have a MPP-Aβ40 concentration of 176.50 pg/ml or below, or high logistic regression p-value of more than 0.5 determined using the MPP-Aβ40 concentration, MMSE(Z) score and Hb concentration of the blood) can be diagnosed as PiB-PET positive (Table 9), indicating that the present method can be advantageously used to determine the accumulation of Aβ in the brain without PET scan.

($β_0$: constant=−15.8345, $β_1$: coefficient of MPP-A1340=−0.062340, $β_2$: coefficient of MMSE(Z)=−1.30872, $β_3$: coefficient of Hb=1.85886, average value of PiB-PET negative-MPP-Aβ40: $x_1$=175.95, average value of PiB-PET negative-MMSE(z): $x_2$=0.20988 and average value of PiB-PET negative-Hb: $x_3$=13.5115; ln(1/1−p)=−1.511910264). The tolerance interval of the criterion (±5% of sensitivity and specificity on the cut off criterion) is listed in table 10 and table 11 (orange, tolerance interval of criterion; red, criterion value; table 11 is larger version of cut-off criterion of table 10). Specifically, the reliable optimal cut off range (based on the tolerance interval of the criterion) was found to be 0.53 to 0.59, which is a value that has increased 194.7% to 224.5% compared to the average p value of the PET negative group. Thus, the subjects who have increased p-value by more than 194.7% to 224.5% compared with the average p-value of PiB-PET negative subjects can be diagnosed as PiB-PET positive. For example, it can be interpreted that the subject with an increase in p-value by less than 194.7% are not determined as PET positive, but the increase by more than 224.5% is determined as PET positive, while it is more reliable that the increase by 194.7% to 224.5% in p value compared to the average p value of PET negative group is used to determine the subject as PET positive

TABLE 9

| Discrimination | Parameters | AUC (%) | Sensitivity (%) | Specificity (%) | Criterion | P-value (Coefficients) | P-value (Area = 0.5) | Increase in AUC (%) after PIC |
|---|---|---|---|---|---|---|---|---|
| | (B) Discrimination ability of single markers | | | | | | | |
| | PIC-Aβ 1-40 | 71.6% | 92.3% | 53.9% | ≤176.50 pg/ml | — | 0.0042 | 1.9% |
| | MMSE(Z) | 76.0% | 65.4% | 88.5% | ≤−1.06 | — | 0.0002 | — |
| | Hemoglobin | 64.4% | 69.2% | 69.2% | >13.60 g/dL | — | 0.0741 | — |
| | (C) Discrimination ability of diverse markers with stepwise procedure | | | | | | | |
| PiB-PET negative vs PiB-PET positive | PIC-Aβ 1-40 MMSE(Z) | 85.9% | 69.2% | 92.3% | >0.65 | 0.0086 0.0010 | <0.0001 | 3.4% |
| | PIC-Aβ 1-40 Hemoglobin | 71.6% | 96.2% | 50.0% | >0.39 | 0.0178 0.0502 (excluded) | 0.0042 | 1.8% |
| | MMSE(Z) Hemoglobin | 83.1% | 73.1% | 88.5% | >0.60 | 0.0010 0.0193 | <0.0001 | — |
| | PIC-Aβ 1-40 MMSE(Z) Hemoglobin | 92.5% | 80.8% | 92.3% | >0.59 | 0.0029 0.0009 0.0071 | <0.0001 | 5.6% |

<3-2-1> The Discrimination of PiB-PET Positive and PiB-PET Negative

The average p-value of PiB-PET negative subjects was fond to be 0.18, which was calculated by formula 1 and 2

TABLE 10

| Criterion | Sensitivity | 95% CI | Specificity | 95% CI | +LR | −LR |
|---|---|---|---|---|---|---|
| ≥0.003376866 | 100.00 | 86.8-100.0 | 0.00 | 0.0-13.2 | 1.00 | |
| >0.062204897 | 100.00 | 86.8-100.00 | 38.46 | 20.2-59.4 | 1.62 | 0.00 |
| >0.064160663 | 96.15 | 80.4-99.9 | 38.46 | 20.2-59.4 | 1.56 | 0.100 |
| >0.16022533 | 96.15 | 80.4-99.9 | 57.69 | 36.9-76.6 | 2.27 | 0.067 |
| >0.176630597 | 92.31 | 74.9-99.1 | 57.69 | 36.9-76.6 | 2.18 | 0.13 |
| >0.221707277 | 92.31 | 74.9-99.1 | 65.38 | 44.3-82.8 | 2.67 | 0.12 |
| >0.239679704 | 88.46 | 69.8-97.6 | 65.38 | 44.3-82.8 | 2.56 | 0.18 |
| >0.378303658 | 88.46 | 69.8-97.6 | 73.08 | 52.2-88.4 | 3.29 | 0.16 |
| >0.405163471 | 84.62 | 65.1-95.6 | 73.08 | 52.2-88.4 | 3.14 | 0.21 |
| >0.532260355 | 84.62 | 65.1-95.6 | 88.46 | 69.8-97.6 | 7.33 | .017 |
| >0.566570038 | 80.77 | 60.6-93.4 | 88.46 | 69.8-97.6 | 7.00 | 0.22 |
| >0.586259895 | 80.77 | 60.6-93.4 | 92.31 | 74.9-99.1 | 10.50 | 0.21 |
| >0.620488654 | 73.08 | 52.2-88.4 | 92.31 | 74.9-99.1 | 9.50 | 0.29 |
| >0.646055644 | 73.08 | 52.2-88.4 | 96.15 | 80.4-99.9 | 19.00 | 0.28 |
| >0.713539231 | 69.23 | 48.2-85.7 | 96.15 | 80.4-99.9 | 18.00 | 0.32 |

TABLE 10-continued

| Crite-rion | Sensi-tivity | 95% CI | Speci-ficity | 95% CI | +LR | −LR |
|---|---|---|---|---|---|---|
| >0.729288525 | 69.23 | 48.2-85.7 | 100.0 | 86.8-100.0 | | 0.31 |
| >0.999863015 | 0.00 | 0.0-13.2 | 100.0 | 86.8-100.0 | | 1.00 |

TABLE 11

| Crite-rion | Sensi-tivity | 95% CI | Speci-ficity | 95% CI | +LR | −LR |
|---|---|---|---|---|---|---|
| >0.53 | 84.62 | 65.1-95.6 | 88.46 | 69.8-97.6 | 7.33 | .017 |
| >0.57 | 80.77 | 60.6-93.4 | 88.46 | 69.8-97.6 | 7.00 | 0.22 |
| >0.59 | 80.77 | 60.6-93.4 | 92.31 | 74.9-99.1 | 10.50 | 0.21 |

Figure 6A:
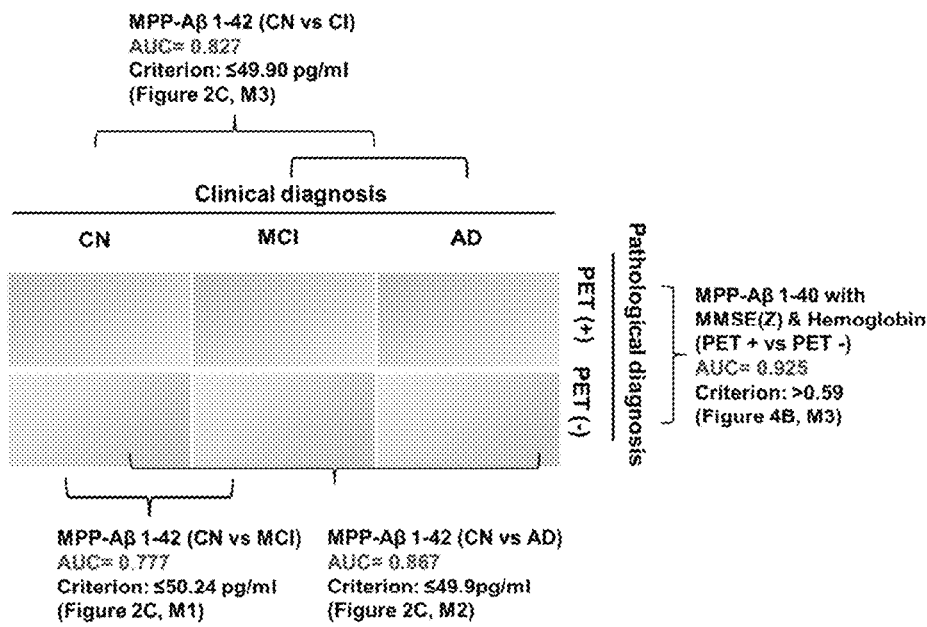
FIGS. 6A and 6B are a schematical representation of determining the accumulation of Aβ in the brain according to one Example of the present disclosure, in which certain cut-off values in the concentration of Aβ42 or Aβ40 determined in the plasma sample treated with the present MPP are used to diagnose clinical cognitive impairment and determine the accumulation of Aβ plaques.
Figure 6B:
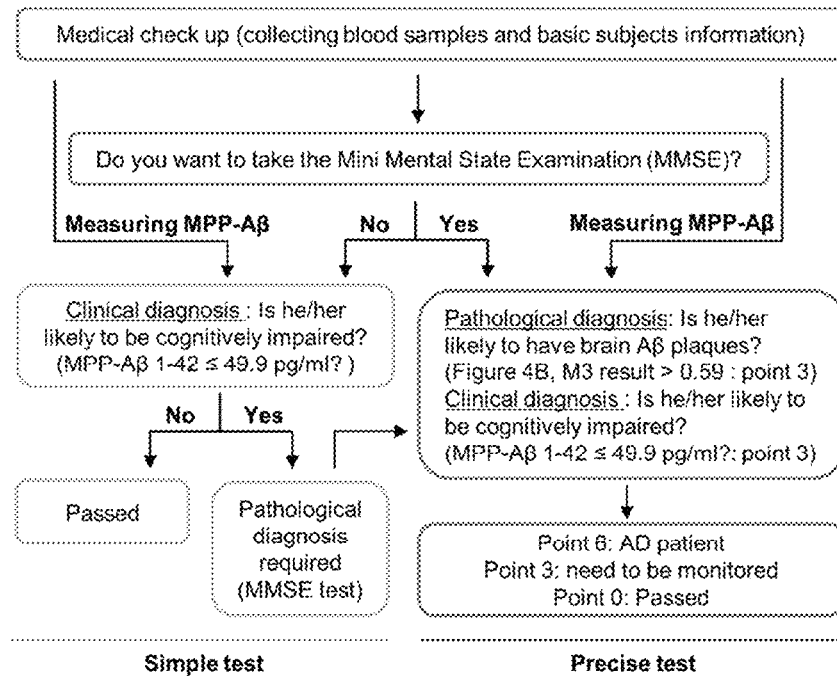

From these, we suggest that pre-incubation of human plasma with the present MPP to determine the concentration of Aβ42 and Aβ40 can be advantageously used to discriminate the cognitive abilities of subjects (CN, MCI and AD groups) or pathological Aβ accumulation in the brains of subjects (PiB-PET positive and PiB-PET negative subjects) by using (FIGS. 6A and 6B).

<Example 4> Measurement of MPP-Treated Plasma Aβ with the Additional Treatment of tris(2-carboxyethyl)phosphine Hydrochloride (TCEP)

Figure 7A:
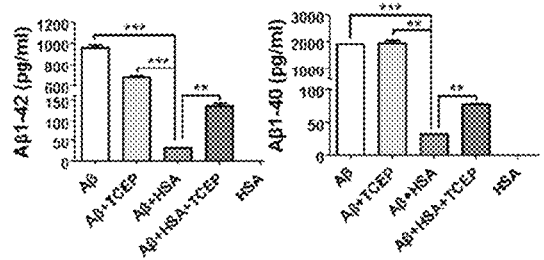
FIGS. 7A and 7B are the results showing the changes in the concentration of Aβ in vitro (FIG. 7A); and in the plasma sample (FIG. 7B), in which the samples were treated with MPP followed by TCEP.
Figure 7B:
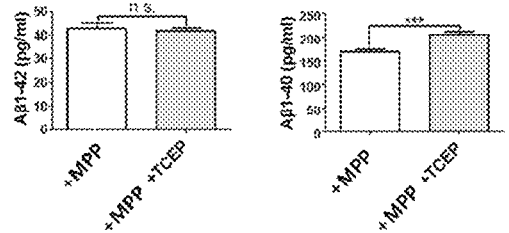

<4-1> Quantification of Plasma Aβ after the Treatment of TCEP on MPP-Treated Plasma As described in <Example 1>, we have used a reducing agent, Tris(2-carboxyethyl)phosphine hydrochloride (TCEP) in addition to MPP at the concentration of 3 mM each to treat the artificially synthesized Aβs (dissolved in diluent buffer including human serum albumin; plasma mimic condition buffer) followed by incubation for 30 minutes. Then the concentration was measured. Consequently, the amount of the Aβ detected was found to be significantly increased in both Aβ42 and Aβ40 by the treatment. This may be explained that TCEP destroyed the 3D structure of HSA, thereby releasing the Aβ bound to the HSA (FIG. 7A). These phenomenon were also observed in the experiments performed with plasma sample Aβ40 (FIG. 7B). Although when the plasma sample was used, the concentration of Aβ42 did not increase by adding TCEP, but it may attribute to the difference between artificially synthesized Aβs and the actual plasma Aβs.

Figure 8:
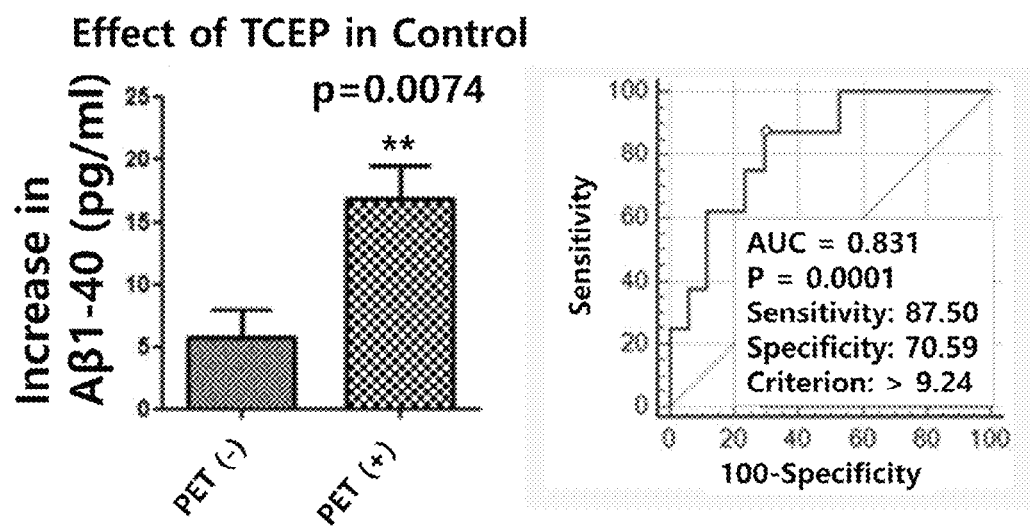
FIG. 8 shows cut-off values to differentiate the PET positive and negative samples, which were determined from the experiments using the normal plasma samples treated with MPP followed by TCEP to increase the sensitivity and specificity of Aβ concentration detection.

<4-2> Relationship Between the Increase in Aβ Concentration by the Treatment with TCEP and the PiB-PET Imaging Data To discriminate between the PiB-PET positive subjects and PiB-PET negative subjects, the concentration of Aβ40 measured in the MPP treated diluent buffer was subtracted from the concentration of Aβ40 measured in the MPP+TCEP treated diluent buffer. It was found that the TCEP has increased Aβ40 concentrations in both PiB-PET positive and negative subjects and we compared the results of the subtraction (the increase in quantity of Aβ40 by the TCEP treatment) between PiB-PET positive subjects and PiB-PET negative subjects. Consequently, the PiB-PET positive subjects among the normal group had a significantly higher increase in Aβ40 by the TCEP treatment. The cut-off criterion of the Aβ increment by treatment with TCEP was >9.24 pg/ml after TCEP treatment, therefore, the subjects who have an increased Aβ concentration by more than 9.24 pg/ml can be diagnosed as a PiB-PET positive subject, with a sensitivity of 87.50% and a specificity of 70.59% (FIG. 8).

Because PiB-PET positive subjects had significantly higher increase in Aβ40 by the TCEP treatment (**p<0.01), it means that if subjects have a higher increase of Aβ40 concentration measured in the plasma treated with MPP+TCEP, he or she may have an increased risk of Aβ accumulation in the brain. Thus, these results suggest that instead of the subjects taking an expensive PiB-PET scan, the concentration of the Aβ determined by the present composition and methods as described herein can be advantageously used to distinguish PiB-PET positive subjects from PiB-PET negative subjects.

INDUSTRIAL APPLICABILITY

The present disclosure can be advantageously used for diagnosis of dementia, cognitive impairment in clinic.

The invention claimed is:

1. A method of diagnosing a cognitive impairment in a subject in need thereof comprising the steps of:
   1) measuring a concentration of Aβ42 in a plasma sample isolated from the subject and a normal control, wherein the sample is pretreated with a composition comprising a protease inhibitor and a phosphatase inhibitor to reduce a standard deviation associated with the measurement; and
   2) determining that the subject is affected with MCI (Mild Cognitive Impairment) with a specificity of at least 65%, when the concentration of Aβ42 in the plasma of the subject is decreased by more than 8.0% compared to the average concentration of Aβ42 measured in the plasma of the normal control.

2. The method of claim 1, wherein in step 2, it is determined that the subject is affected with MCI with a specificity of at least 65% and a sensitivity of at least 75%, when the concentration of Aβ42 in the plasma of the subject is decreased by 8.0% to 11.0% compared to the average concentration of Aβ42 measured in the plasma of the normal control.

3. A method of diagnosing a cognitive impairment in a subject in need thereof comprising the steps of:
   1) measuring a concentration of Aβ42 in a plasma sample isolated from the subject and a normal control, wherein the sample is pretreated with a composition comprising a protease inhibitor and a phosphatase inhibitor to reduce a standard deviation associated with the measurement; and
   2) determining that the subject is affected with AD (Alzheimer's disease) with a specificity of at least 70% when the concentration of Aβ42 in the plasma of the subject is decreased by more than 9.0% compared to the average concentration of Aβ42 measured in the plasma of the normal control.

4. The method of claim 3, wherein in step 2, it is determined that the subject is affected with AD with a specificity of at least 70% and a sensitivity of at least 80%, when the concentration of Aβ42 in the plasma of the subject is decreased by 9.0% to 21.0% compared to the average concentration of Aβ42 measured in the plasma of the normal control.

5. A method of diagnosing CI (cognitive impairment) in a subject in need thereof comprising the steps of:
  1) measuring a concentration of Aβ42 in a plasma sample isolated from the subject and a normal control, wherein the sample is pretreated with a composition comprising a protease inhibitor and a phosphatase inhibitor to reduce a standard deviation associated with the measurement; and
  2) determining that the subject is affected with CI (MCI and AD) with a specificity of at least 65%, when the concentration of Aβ42 in the plasma of the subject is decreased by more than 8.5% compared to the average concentration of Aβ42 measured in the plasma of the normal control.

6. The method of claim 5, in step 2, it is determined that the subject is affected with CI (MCI and AD) with a specificity of at least 65% and a sensitivity of at least 75%, when the concentration of Aβ42 in the plasma of the subject is decreased by 8.0% to 10% compared to the average concentration of Aβ42 measured in the plasma of the normal control.

* * * * *